United States Patent
Verkuijl

(10) Patent No.: US 9,353,041 B2
(45) Date of Patent: May 31, 2016

(54) ESTER FORMATION OF FATTY ACID AND HYDROXYCARBOXYLIC ACID

(71) Applicant: PURAC BIOCHEM BV, Gorinchem (NL)

(72) Inventor: Bastiaan Jeroen Victor Verkuijl, Maarn (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 14/406,556

(22) PCT Filed: Jun. 14, 2013

(86) PCT No.: PCT/EP2013/062391
§ 371 (c)(1),
(2) Date: Dec. 9, 2014

(87) PCT Pub. No.: WO2013/189853
PCT Pub. Date: Dec. 27, 2013

(65) Prior Publication Data
US 2015/0141683 A1    May 21, 2015

Related U.S. Application Data

(60) Provisional application No. 61/660,836, filed on Jun. 18, 2012.

(30) Foreign Application Priority Data

Jun. 18, 2012 (EP) ..................................... 12172373

(51) Int. Cl.
*C07C 67/03* (2006.01)

(52) U.S. Cl.
CPC ..................................... *C07C 67/03* (2013.01)

(58) Field of Classification Search
CPC ........ C07C 67/03; C07C 69/24; C07C 69/68; C07C 69/675; C11C 3/003
See application file for complete search history.

(56) References Cited

U.S. PATENT DOCUMENTS 2,733,252 A    1/1956   Thompson et al.
4,371,561 A *  2/1983   Forsythe ........................ 426/653
5,872,268 A    2/1999   Kasori et al.

OTHER PUBLICATIONS

International Search Report issued in International Patent Application No. PCT/EP2013/062391 dated Aug. 13, 2013.
International Written Opinion issued in International Patent Application No. PCT/EP2013/062391 dated Aug. 13, 2013.

* cited by examiner

*Primary Examiner* — Yate K Cutliff
(74) *Attorney, Agent, or Firm* — Oliff PLC

(57) ABSTRACT

The present invention relates to a process for the transesterification of a fatty acid ester of a lower alcohol and a salt of hydroxycarboxylic acid without making use of organic solvents. The process can also be carried out without added anionic surface active agents.

20 Claims, No Drawings

ESTER FORMATION OF FATTY ACID AND HYDROXYCARBOXYLIC ACID

The present invention relates to a process for the preparation of a salt of a fatty acid ester of hydroxycarboxylic acid, in particular a salt of a fatty acid ester of lactic acid which is also called a lactylate. Salts of fatty acid esters of hydroxycarboxylic acids are known to be useful as emulsifier in food applications, as emulsifier in cosmetic applications for home and personal care and as growth promoter in Animal Health.

Such a compound can be prepared by direct esterification of lactic acid and a fatty acid as has been described in U.S. Pat. No. 2,733,252. An improved process has been described in U.S. Pat. No. 5,872,268, wherein a fatty acid ester of a lower alcohol and a salt of hydrocarboxylic acid are subjected to ester interchange. This process, however, requires the presence of an organic solvent and a nonionic or anionic surface active agent.

According to the present invention a process has been found which makes use of an ester interchange between a fatty acid ester of a lower alcohol and a salt of hydrocarboxylic acid without making use of organic solvents. Also added anionic surface active agents are not necessary.

The process has the advantage that there is a high conversion into the salt of the required fatty acid ester of hydroxycarboxylic acid resulting in a high amount of the desired ester.

The reaction also selectively moves towards the fatty acid ester of a monomeric hydroxycarboxylic acid (e.g. 1-lactylate or monolactylate) and in the resulting end product no azeotropic mixture with free fatty acids is formed.

Furthermore, the process is more convenient in that there is less blocking of accumulating fatty acids in the equipment.

The present invention pertains to a process for the preparation of a salt of a fatty acid ester of hydroxycarboxylic acid which comprises heating a salt of hydroxycarboxylic acid with a catalyst in admixture with a C8-C24 fatty acid (i.e. having 8 to 24 carbon atoms) ester of a lower alcohol having 1-4 carbon atoms at a temperature at which there exists a liquid phase and subjecting the mixture to ester interchange whereby the temperature of the process is kept at or below the boiling point of the C8-C24 fatty acid ester of a lower alcohol having 1-4 carbon atoms.

This process solves the disadvantages mentioned here above for the hitherto known processes. The process does not require the use or presence of an organic solvent in an amount necessary to form a liquid state as the salt of the hydroxycarboxylic acid in admixture with the fatty acid ester is in its liquid state. The process also does not need the use of a nonionic or anionic surface active agent in an amount necessary to enhance or cause mixing because spontaneous mixing of the reactants occurs during the reaction.

Hereinafter, the present invention is further described in detail.

The type of hydroxycarboxylic acid salt used according to the present invention can be any type of hydroxycarboxylic acid salt inasfar as it can form a liquid mixture or dispersion with the fatty acid ester of a lower alcohol. Thereto, hydrocarboxylic acid as used herein means a mono or di carboxylic acid molecule having 2-4 carbon atoms and 1-3 hydroxyl groups. Examples are lactic acid, malic acid and tartaric acid. With the term hydroxycarboxylic acid salt is, in addition to the regular salts of hydroxycarboxylic acid, also meant a cyclic carboxylic acid. Preferred are metal salts, in particular alkaline metal salts or alkaline earth metal salts. The preferred hydroxycarboxylic acid is lactic acid. Most preferred are sodium or potassium lactate or magnesium or zinc lactate. Even more preferred are sodium or potassium lactate. The preferred cyclic hydroxycarboxylic acid is lactide.

The type of alkyl ester constituting the fatty acid moiety of the fatty acid ester of lower alcohol according to the present invention preferably has a boiling point above the melting point of the hydroxycarboxylic acid salt, to keep the whole process liquid. The alkyl ester molecule contains two alkyl groups: the 'acid' part can be any length, as long as it is liquid at the desired reaction temperature. The 'alcohol' part needs to be sufficiently short, to be able to evaporate upon reaction.

Examples of fatty acids include saturated or unsaturated fatty acids with 8-24 carbon atoms. Also branched chain fatty acids or one or more hydroxyl groups may be used. Examples of such fatty acids are caprylic acid, capric acid, lauric acid, myristic acid, palmitic acid stearic acid, oleic acid linoleic acid, alpha linolenic acid, ricinolleic acid, petroselinic acid, arachidic acid and behenic acid. Preferred fatty acids are fatty acids with 8-18 carbon atoms (C8-C18). More preferred are fatty acids with 12-18 carbon atoms (C12-C18), more preferred with 12-14 carbon atoms (C12-C14). Most preferred is a fatty acid with 12 carbon atoms.

As the lower alcohol moiety of the fatty acid ester of lower alcohol in the present invention, a primary alcohol having 1-4 carbon atoms (such as methanol, ethanol, propanol or butanol) or a mixture thereof may be used. These alcohols can easily be removed in the course of the transesterification reaction by vaporization. Preferred alcohols are methanol and ethanol or a mixture thereof.

Preferred fatty acid ester of a lower alcohol is methyl laurate. Preferred hydroxycarboxylic acid salt is sodium lactate.

The reaction process can also be carried out with mixtures of different C8-C24 fatty acid esters of the lower alcohol having 1-4 carbon atoms. Preferred are mixtures with fatty acids with 12, 14, 16 and/or 18 carbon atoms. The lower alcohol preferably has 1-2 carbon atoms, most preferably is methanol.

In one embodiment the salt of the hydroxycarboxylic acid is first heated with the catalyst to a temperature equal to or above the melting temperature of the hydroxycarboxilic acid salt and then the C8-C24 fatty acid ester of the lower alcohol is added. Thereafter the mixture is subjected to the transesterification reaction at a temperature as indicated above i.e. at or between the melting point of the hydroxycarboxylic acid salt and the boiling point of the C8-C24 fatty acid ester of a lower alcohol having 1-4 carbon atoms. Alternatively, the catalyst can also be added in a later stage e.g. with the addition of the C8-C24 fatty acid ester.

The temperature of the reaction is chosen such that the mixture of the two reagents i.e. the salt of hydroxycarboxylic acid and the C8-C24 fatty acid ester of a the lower alcohol having 1-4 carbon atoms are in the liquid stage. With the term liquid stage or liquid phase it is meant that the mixture is a real liquid, or is a dispersion, suspension, emulsion, colloid or the like.

As mentioned here above the process does not require the presence of an organic solvent. Added nonionic or anionic surface active agent can be present, but may also be absent. In one embodiment less than 15 mol % based on the salt of the hydroxycarboxylic acid may be present. In another embodiment less than 10 mol % of surfactant is present. In yet another embodiment less than 5 mol % of surfactant is present. In another embodiment no added nonionic or anionic surface active agents are present.

The preferred temperature range of the transesterification reaction is between the melting temperature of the salt of the hydroxycarboxylic acid and the boiling point of the C8-C24 fatty acid ester of a lower alcohol having 1-4 carbon atoms.

Almost any sufficiently strong alkali catalyst can be used in the present reaction. The catalyst should be able to deprotonate the alcohol group of the hydroxycarboxylic acid. Preferably, the catalyst used in the present reaction has the general formula alkali-OR wherein R stands for H or (C1-C3)alkyl. Preferably, the alkyl group is methyl. The metal moiety of the alkali catalyst is preferably the same as the metal moiety of the salt of hydroxycarboxylic acid in the reaction. Preferably this is sodium. The amount of catalyst to be added is from 0.01 to 20 mol % based on the fatty acid ester of lower alcohol. In case lactide is used as hydroxycarboxylic acid source a higher amount of alkali might be added to convert the lactide to lactate.

The content of salt of hydroxycarboxylic acid is from 0.2 to 20, preferably from 0.5-3 mols per mol of the fatty acid ester of a lower alcohol having 1-4 carbon atoms.

In a typical reaction, the salt of hydroxycarboxylic acid is mixed with the catalyst and heated to a temperature such that the mixture will melt. Preferably the temperature is in the range of 160-200° C. Sodium lactate has a melting point of 161-162° C. Thus, if sodium lactate is used as the source of the hydroxycarboxylic acid salt the temperature should be preferably above this melting point range. Water or alkanol (e.g. methanol) arising through the reaction will be removed from the reaction mixture by vaporization, creating vacuum or by distillation. Then the C8-C24 fatty acid ester of a lower alcohol having 1-4 carbon atoms is added slowly. A one phase, milky type of reaction mixture will be formed quickly. The reaction will be continued at the high temperature and methanol will be removed by creating a vacuum or bubbling through an inert gas. The reaction can be monitored e.g. by TLC and/or GC. If the reaction is completed, the reaction can be stopped by cooling down the reaction mixture.

A condenser or distillation column can be attached to the reaction vessel so that byproduced water and alcohol can be removed from the vessel during the reaction. Furthermore, a vacuum can be applied to the reaction mixture to expulse the alcohol more rapidly and thus bring the reaction faster to completion.

It should be emphasized that in accordance with the present invention the transesterification reaction is carried out without the presence of a solvent. After the reaction, the resulting product can be neutralized if needed with a (weak) acid or any amphoteric compound, like water or sodium bicarbonate.

The salt of fatty acid ester of hydroxycarboxylic acid obtained according to the present invention may be optionally purified by washing, recrystallization, extraction with solution or the like to obtain a product having a higher purity.

The present invention will be elucidated with the following examples, without being limited thereto or thereby.

EXAMPLES

Example 1

Methyl Laurate, Sodium Lactate and Catalyst are used in a molar ratio of ML:SL:C=1.0:1.2:0.1.

In a pre-dried distillation set-up with a nitrogen gas inlet through the reaction medium, sodium lactate (6.2 g) and catalyst (0.25 g of sodium methoxide) are added. The reaction mixture is heated to a temperature of 160° C. The sodium lactate will melt. Water or methanol will be distilled off. After this, the methyl laurate (10 g) is added drop wise in the course of 10 minutes. Initially, a 2 phase system is there, but quickly, a one phase, milky type of reaction mixture is formed. The reaction is continued and MeOH is distilled off continuously. The temperature is increased gradually to 200° C. and vacuum is applied and gradually brought down to 50 mbar to keep alcohol distillation constant. The reaction mixture is cooled down when the reaction is completed. An off-white to light brown, highly viscous paste is obtained. GC (rel. Area): methyl laurate 19.0; sodium lactylate 425.0.

Example 2

Methyl Laurate, Lactide and sodium hydroxide are used in a molar ratio of ML:Lact:NaOH=1.0:1.2:2.64.

NaOH (2.46 g) was weighed out in a flask under a continuous nitrogen flow. Lactide (4.0 g) was added, along with a few drops of water. After a violent reaction, the temperature was put to 130° C. After a few hours, the solution turned into a yellow paste. It was cooled to 90° C. and methyl laurate was added dropwise. The temperature was set at 150° C. and the reaction was stirred overnight. A light yellow, highly viscous paste was obtained. GC (rel. Area): methyl laurate 86.5; sodium lactylate 464.4.

Example 3

Methyl Caprate, Sodium Lactate and Catalyst were used in a molar ratio of MC:SL:C=1.0:1.2:0.05. In a pre-dried distillation set-up with mechanical stirrer, sodium lactate (54 g) and methyl caprate (75 g) were added. The reaction mixture was heated to a temperature of 160° C. The sodium lactate melted and a two-phase liquid-liquid system was observed. The catalyst (1.3 g of sodium methoxide) was added. Quickly, a one phase, milky type of reaction mixture was formed. The reaction was continued and MeOH was distilled off continuously. The temperature was increased gradually to 190° C. Vacuum was applied and gradually brought down from 800 to 100 mbar to keep alcohol distillation constant, during a course of 8 hours. The reaction mixture was cooled down when the reaction was completed. An off-white to brown, highly viscous paste is obtained. GC revealed C10 1-lactylate formation.

Example 4

Methyl Stearate, Sodium Lactate and Catalyst are used in a molar ratio of ML:SL:C=1.0:1.2:0.1. In a pre-dried distillation set-up with mechanical stirrer, sodium lactate (45 g), methyl stearate (100 g) and sodium methoxide (1.8 g) were added. The reaction mixture was heated to a temperature of 200° C. and the vacuum was set to 50 mbar. The sodium lactate melted and a two-phase liquid-liquid system was observed. Quickly, a one phase, milky type of reaction mixture was formed. The reaction was continued and MeOH was distilled off continuously during a course of 8 hours. The reaction mixture was cooled down and an off-white to brown, highly viscous paste was obtained. GC revealed C18 1-lactylate formation.

The invention claimed is:

1. A process for the preparation of a salt of a fatty acid ester of hydroxycarboxylic acid which comprises heating a salt of hydroxycarboxylic acid with a catalyst in admixture with a C8-C24 fatty acid ester of a lower alcohol having 1-4 carbon atoms at a temperature at which there exists a liquid phase and subjecting the mixture to ester interchange whereby the temperature of the process is kept at or below the boiling point of the C8-C24 fatty acid ester of a lower alcohol having 1-4 carbon atoms, wherein the temperature is in the range of 160-200° C.

2. The process according to claim 1 wherein the heating of a salt of hydroxycarboxylic acid with a catalyst in admixture with a C8-C24 fatty acid ester of a lower alcohol having 1-4 carbon atoms occurs in the absence of an organic solvent.

3. The process of claim 1 wherein the temperature is kept between the melting temperature of the salt of hydroxycarboxylic acid and the boiling point of the C8-C24 fatty acid ester of a lower alcohol having 1-4 carbon.

4. The process of claim 1 wherein said hydroxycarboxylic acid is lactic acid.

5. The process according to claim 1 wherein said C8-C24 fatty acid ester of a lower alcohol having 1-4 carbon atoms is a C8-C18 fatty acid ester of a lower alcohol having 1-4 carbon atoms.

6. The process of claim 1 wherein the lower alcohol of said C8-C24 fatty acid ester has 1-2 carbon atoms.

7. The process of claim 6 wherein the C8-C24 fatty acid ester of a lower alcohol having 1-4 carbon atoms is methyl laurate.

8. The process of claim 1 wherein said catalyst is of the following formula:

M-OR wherein

M is an alkali metal, and

R is H or Me.

9. The process of claim 4 wherein said salt of hydroxycarboxylic acid is sodium lactate.

10. The process of claim 1 wherein the molar ratio of salt hydroxycarboxylic acid to the C8-C24 fatty acid ester of a lower alcohol having 1-4 carbon atoms is from 0.2 to 20 mols per mol.

11. The process according to claim 1 wherein water and the lower alcohol are evaporated.

12. The process according to claim 1, wherein the catalyst is NaOH or NaOMe.

13. A process for the preparation of a salt of a fatty acid ester of hydroxycarboxylic acid which comprises heating a salt of hydroxycarboxylic acid with a catalyst in admixture with a C8-C24 fatty acid ester of a lower alcohol having 1-4 carbon atoms at a temperature at which there exists a liquid phase and subjecting the mixture to ester interchange whereby the temperature of the process is kept at or below the boiling point of the C8-C24 fatty acid ester of a lower alcohol having 1-4 carbon atoms, wherein the heating of a salt of hydroxycarboxylic acid with a catalyst in admixture with a C8-C24 fatty acid ester of a lower alcohol having 1-4 carbon atoms occurs in the absence of an organic solvent.

14. The process of claim 13, wherein said hydroxycarboxylic acid is lactic acid.

15. The process of claim 13, wherein said catalyst is of the following formula:

M-OR wherein

M is an alkali metal, and

R is H or Me.

16. The process of claim 13, wherein the temperature is kept between the melting temperature of the salt of hydroxycarboxylic acid and the boiling point of the C8-C24 fatty acid ester of a lower alcohol having 1-4 carbon.

17. The process of claim 13, wherein the reaction temperature is in the range of 160-200° C.

18. The process of claim 13, wherein water and the lower alcohol are evaporated.

19. The process of claim 13, wherein the molar ratio of salt hydroxycarboxylic acid to the C8-C24 fatty acid ester of a lower alcohol having 1-4 carbon atoms is from 0.2 to 20 mols per mol.

20. A process for the preparation of a salt of a fatty acid ester of hydroxycarboxylic acid which comprises heating a salt of hydroxycarboxylic acid with a catalyst in admixture with a C8-C24 fatty acid ester of a lower alcohol having 1-4 carbon atoms at a temperature at which there exists a liquid phase and subjecting the mixture to ester interchange whereby the temperature of the process is kept at or below the boiling point of the C8-C24 fatty acid ester of a lower alcohol having 1-4 carbon atoms, wherein the heating of a salt of hydroxycarboxylic acid with a catalyst in admixture with a C8-C24 fatty acid ester of a lower alcohol having 1-4 carbon atoms occurs in the absence of an amount of an organic solvent necessary to form a liquid state.

\* \* \* \* \*